United States Patent [19]
Rolland et al.

[11] Patent Number: 6,040,295
[45] Date of Patent: *Mar. 21, 2000

[54] FORMULATED NUCLEIC ACID COMPOSITIONS AND METHODS OF ADMINISTERING THE SAME FOR GENE THERAPY

[75] Inventors: Alain Rolland, Houston; Russell J. Mumper, The Woodlands, both of Tex.

[73] Assignee: Genemedicine, Inc., Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/372,213

[22] Filed: Jan. 13, 1995

[51] Int. Cl.[7] .................................................. A61K 48/00
[52] U.S. Cl. ........................... 514/44; 424/484; 424/486; 424/497; 424/450; 435/320.1; 435/455; 435/458; 536/23.1
[58] Field of Search ............................... 514/44; 424/484, 424/486, 497, 450; 435/455, 458, 320.1; 536/23.1

[56] References Cited

U.S. PATENT DOCUMENTS

| | | | |
|---|---|---|---|
| 5,512,435 | 4/1996 | Stone et al. | 435/6 |
| 5,531,925 | 7/1996 | Landh et al. | 252/299.01 |
| 5,573,934 | 11/1996 | Hubbell et al. | 435/177 |
| 5,578,325 | 11/1996 | Domb et al. | 424/501 |
| 5,580,575 | 12/1996 | Unger et al. | 424/450 |
| 5,583,034 | 12/1996 | Green et al. | 435/325 |
| 5,591,721 | 1/1997 | Agrawal et al. | 514/44 |
| 5,770,580 | 6/1998 | Ledley et al. | 514/44 |

FOREIGN PATENT DOCUMENTS

| | | |
|---|---|---|
| WO 90/11092 | 4/1990 | WIPO . |
| 9424983 | 11/1994 | WIPO . |

OTHER PUBLICATIONS

Mumper et al.Pharmaceutical Res., vol. 13, 5, pp. 701–709, 1996.
Kabanov et al., Biopolymers, 1991, 31/12, 1437–1443.
Monsigny et al., Ad. Drug Delivery Reviews, 14:1–24, 1994.
Ledley, Hum. Gene. Ther., 6: 1129–1144, 1995.
Kuo et al., Critical Reviews in Eukaryotic Expression 6, 1: 59–73, 1996.
Salzman et al., Critical Reviews in Eukaryotic Gene Expression, vol. 6, 1, pp. 59–73, 1996.
Monsigny et al., Advanced Drug Delivery Reviews, vol. 14, pp. 1–24, 1994.
Petrak, Pharmaceutical Particulate Carriers, 1993, pp. 275–293.
Hung et al., Gene Therapy, vol. 1, 1: pp. 64–69, 1994.
Ledley (1995) Human Gene Therapy 6: 1129–1144.
Papisov (1995) Adv. Drug Del. Rev. 16: 127–139.
Ewel et al. (1992) Cancer Research 52: 3005–3010.
Biswas et al. (1994) Journal of Biotechnology 32: 1–10.
Szoka et al. (1993) Bioconjugate Chem. 4, 372–379.
Duncan et al. (1992) Anti Cancer Drugs, 3: 175–210.
Park et al. (1993) Advanced Drug Delivery Reviews, 11: 59–84.
Bennett et al., "Inhibition of Vascular Smooth Muscle Cell Proliferation in Vitro and in Vivo by c–myc Antisense Oligodeoxynucleotides," *J. Clin. Invest.* 93(2):820–828 (1940).
Caso et al., "Transfection in *Micromonospora* spp.," *Applied and Environmental Microbiology* 53(10):2544–2547 (1987).
Chemla et al., "Effects of Antisense Oligonucleotides on Myointimale Hyperplasia in a Model of Abdominal Aortic Trauma in the Rat," *Archives des Maladies Due Coeur Et Des Vaisseaux* 88(3):381–389 (1995).
Curiel et al., "High–Efficiency Gene Transfer Mediated by Adenovirus Coupled to DNA–Polylysine Complexes," *Human Gene Therapy* 3:147–154 (1992).
"Reporter System Using Chloramphenicol Acetyltransferase," in *Current Protocols in Molecular Biology*, Supplement 29, Chapter 9, Unit 9.6A, pp. 9.6.5–9.6.6 (1993).
Davis et al., "Direct Gene Transfer into Skeletal Muscle In Vivo: Factors Affecting Efficiency of Transfer and Stability of Expression," *Human Gene Therapy* 4:151–159 (1993).
Edelman et al., "c–myc in Vasculoproliferative Disease," *Circulation Research* 76(2):176–182 (1995).
Felgner et al., "Lipofection: A Highly Efficient, Lipid–mediated DNA–transfection Procedure," *Proc. Natl. Acad. Sci. USA* 84:7413–7417 (1987).
Fraley et al., "Introduction of Liposome Encapsulated SV40 DNA into Cells," *J. Biol. Chem.* 225(21):10431–10435 (1980).
Fulton et al., "Luminescent Reporter Gene Assays for Luciferase and $\mu$–Galactosidase Using a Liquid Scintillation Counter," *BioTechniques* 14(5):762–763 (1993).
Jain and Magrath, "A Chemiluminescent Assays for Quantitation of $\mu$Galactosidase in the Femtogram Range: Application of Quantitation of $\mu$–Galactosidase in lacZ–Transfected Cells," *Analytical Biochemistry* 199:119–124 (1991).
Klebe et al., "Uptake by Cells of Nucleic Acids Promoted by Compounds Sharing the Pleiotropic Effects of Poly(Ethylene Glycol)," *Teratogenesis, Carcinogenesis and Mutagenesis* 6(3):245–250 (1986).
March et al., "Facilitation of Adenoviral Gene Delivery by Poloxamer 407," *Proceed. Intern. Symp. Control. Rel. Bioact. Mater.* 21:348 (1994).
Mumper et al., "Interactive Polymeric Gene Delivery Systems for Enhanced Muscle Expression," *Pharmaceutical Research* 12(9):S80 at abstract 2005 (1995).

(List continued on next page.)

*Primary Examiner*—Bruce R. Campbell
*Assistant Examiner*—Dave Trong Nguyen
*Attorney, Agent, or Firm*—Lyon & Lyon LLP

[57] ABSTRACT

Compositions and methods for administering nucleic acid compositions in vitro to cells in culture or in vivo to an organism whereby the uptake of nucleic acids is enhanced are provided. Various compositions, including thermoreversible gels, are utilized to increase the viscosity of an administered nucleic acid formulation, thereby prolonging the localized bioavailability of the administered nucleic acid.

9 Claims, 7 Drawing Sheets

OTHER PUBLICATIONS

Nguyen et al., "Firefly Luciferase Luminescence Assays Using Scintillation Counters for Quantitation in Transfected Mammalian Cells," *Analytical Biochemistry* 171:404–408 (1988).

Shaper et al., "Male Germ Cell Expression of Murine $\mu$4–Galactosylatransferase: A 796–base pair genomic region containing two cAMP–responsive elements (CRE)–like elements, mediates expression in transgenic mice," *J. Biol. Chem.* 269:25165–25171 (1994).

Uglea and Dumitru–Medvichi, "Ch. 15—Medical Applications of Synthetic Oligomers," in *Polymeric Biomaterials*, edited by Severian Dumitriu, Marcel Dekker, Inc., New York, pp. 725–747 (1994).

U.S. Application No. 07/913,669, filed Jul. 14, 1992.

Wagner et al., "Transferrin–polycation Conjugates as Carriers for DNA Uptake Into Cells," *Proc. Natl. Acad. Sci. USA* 87:3410–3414 (1990).

Weith et al., "Synthesis of Cellulose Derivatives Containing the Dihydropxyboryl Group and a Study of Their Capacity to Form Specific Complexes with Sugars and Nucleic Acid Components," *Biochemistry* 9(22):4396–4401 (1970).

Young et al., "Selective Inactivation of Eukaryotic $\mu$–Galactosidase in Assays for Inhibitors of HIV–1 TAT Using Bacterial $\mu$–Galactosidases as a Reporter Enzyme," *Analytical Biochemistry* 215:24–30 (1993).

FORMULATED NUCLEIC ACID COMPOSITIONS AND METHODS OF ADMINISTERING THE SAME FOR GENE THERAPY

BACKGROUND OF THE INVENTION

This invention relates to compositions and methods for the introduction of a formulated nucleic acid into a cell for the expression of a peptide or polypeptide. It is useful for in vitro transfections and in vivo for gene therapy, for among other things administration of therapeutic proteins, polypeptides and peptides and for vaccination.

Non-viral administration of nucleic acid in vivo has been accomplished by a variety of methods. These include lipofectin/liposome fusion: Proc. Natl. Acad. Sci., Volume 84, pp. 7413–7417 (1993); polylysine condensation with and without adenovirus enhancement: Human Gene Therapy, Volume 3, pp. 147–154 (1992); and transferrin-:transferrin receptor delivery of nucleic acid to cells: Proc. Natl. Acad. Sci., Volume 87, pp. 3410–3414 (1990). The use of a specific composition consisting of polyacrylic acid has been disclosed in WO 94/24983. Naked DNA has been administered as disclosed in WO 90/11092.

An important goal of gene therapy, as an initial step in the process of ultimately obtaining expression of a product encoded by a nucleic acid, is to effect the uptake of nucleic acid by cells. Uptake of nucleic acid by cells is dependent on a number of factors, one of which is the length of time during which a nucleic acid is in proximity to a cellular surface. For instance, after intramuscular (i.m.) administration of plasmid DNA in buffer, a marked reduction in gene expression is observed if the muscle is massaged, presumably due to DNA leakage out of the muscle either directly or via lymphatic vessels (Human Gene Therapy 4:151–159; 1993). Accordingly, it would be desirable to formulate nucleic acids with compounds which would retard the rate at which nucleic acids diffuse or are carried away from a site at which cellular uptake of the nucleic acid is desired. Further, these compounds would be suitable for administration to an organism by means such as injection while maintaining or regaining the physical characteristics necessary to increase cellular uptake of nucleic acids.

SUMMARY OF THE INVENTION

This invention features compositions and methods for enhancing the administration to and uptake of nucleic acids by an organism. An efficient strategy for enhancing nucleic acid delivery in vivo is to maintain the administered nucleic acid at the target site in order to further increase its cellular uptake. Also, for in vitro administration increasing the effective concentration of the nucleic acid at the cell surface should increase the efficiency of transfection. The compositions of the present invention which are used to administer nucleic a acid comprise a compound which prolongs the localized bioavailability of the nucleic acid when administered to an organism or in vitro in cell culture.

By "prolong the localized bioavailability of a nucleic acid" is meant that a nucleic acid when administered to an organism in a composition comprising such a compound will be available for uptake by cells for a longer period of time than if administered in a composition without such a compound, for example when administered in a less viscous formulation such, as a saline solution. This increased availability of nucleic acid to cells could occur, for example, due to increased duration of contact between the composition containing the nucleic acid and a cell or due to protection of the nucleic acid from attack by nucleases. The compounds which prolong the localized bioavailability of a nucleic acid are suitable for internal administration.

By "suitable for internal administration" is meant that the compounds are suitable to be administered within the tissue of an organism, for example within a muscle or within a joint space, intradermally or subcutaneously. Other forms of administration which may be utilized are topical, oral, pulmonary, nasal and mucosal; for example, buccal, vaginal or rectal.

By "nucleic acid" is meant both RNA and DNA including: cDNA, genomic DNA, plasmid DNA or condensed nucleic acid, nucleic acid formulated with cationic lipids, nucleic acid formulated with peptides, cationic polymers, RNA or mRNA. In a preferred embodiment, the nucleic acid administered is plasmid DNA which comprises a "vector".

A "vector" is a nucleic acid molecule incorporating sequences encoding therapeutic product(s) as well as, various regulatory elements for transcription, translation, transcript stability, replication, and other functions as are known in the art. A "transcript stabilizer" is a sequence within the vector which contributes to prolonging the half life (slowing the elimination) of a transcript. "Post-translational processing" means modifications made to the expressed gene product. These may include addition of side chains such as carbohydrates, lipids, inorganic or organic compounds, the cleavage of targeting signals or propeptide elements, as well as the positioning of the gene product in a particular compartment of the cell such as the mitochondria, nucleus, or membranes. The vector may comprise one or more genes in a linear or circularized configuration. The vector may also comprise a plasmid backbone or other elements involved in the production, manufacture, or analysis of a gene product. An "expression vector" is a vector which allows for production of a product encoded for by a nucleic acid sequence contained in the vector. For example, expression of a particular growth factor protein encoded by a particular gene. A "DNA vector" is a vector whose native form is a DNA molecule. A "viral vector" is a vector whose native form is as the genomic material of a viral particle. A "gene product" means products encoded by the vector. Examples of gene products include mRNA templates for translation, ribozymes, antisense RNA, proteins, glycoproteins, lipoproteins and phosphoproteins. The nucleic acid may be associated with a targeting ligand to effect targeted delivery. A "targeting ligand" is a component of the carrier or vehicle which binds to receptors, with an affinity for the ligand, on the surface or within compartments of a cell for the purpose of enhancing uptake or intracellular trafficking of the vector. Tris-galactosyl residues, carnitine derivatives, mannose-6-phosphate, monoclonal antibodies, peptide ligands, and DNA-binding proteins represent examples of targeting ligands which can be used to enhance uptake. "Targeted delivery" involves the use of targeting ligands which specifically enhance translocation of a nucleic acid to specific tissues or cells. A "target" is a specific organ, tissue, or cell for which uptake of a vector and expression of a gene product is intended. "Uptake" means the translocation of the vector from the extracellular to intracellular compartments. This can involve receptor mediated processes, fusion with cell membranes, endocytosis, potocytosis, pinocytosis or other translocation mechanisms. The vector may be taken up by itself or as part of a complex. "Binding" is an intermediate step in uptake of some complexes involving a high-affinity interaction between a targeting ligand and a surface receptor on a target cell. "Intracellular trafficking" is the translocation of the vector within the cell from the point of uptake to the nucleus where expression of a gene product takes place. Alternatively, cytoplasmic expression of a nucleic acid construct utilizing, for example, a T7 polymerase system may be accomplished. Various steps in intracellular trafficking include endosomal release and compartmentalization of the vector within various extranuclear compartments, and nuclear entry. "Endosomal release" is the egress of the vector from the endosome after endocytosis. This is an essential and potentially rate limiting step in the trafficking of vectors to the nucleus. A lytic peptide may be used to assist in this process. A "lytic peptide" is a peptide which functions alone or in conjunction with another compound to penetrate the membrane of a cellular compartment, particularly a lysosomal or endosomal compartment, to allow the escape of the contents of that compartment to another cellular compartment such as the cytosolic and/or nuclear compartment. "Compartmentalization" is the partitioning of vectors in different compartments within a defined extracellular or intracellular space. Significant extracellular compartments may include, for example, the vascular space, hair follicles, interstitial fluid, synovial fluid, cerebral spinal fluid, thyroid follicular fluid. Significant intracellular compartments may include endosome, potosome, lysosome, secondary lysosome, cytoplasmic granule, mitochondria, and the nucleus. "Nuclear entry" is the translocation of the vector across the nuclear membrane into the nucleus where the gene may be transcribed. "Elimination" is the removal or clearance of materials (vectors, transcripts, gene products) from a specific compartment over time. This term may be used to reflect elimination from the body, the vascular compartment, extracellular compartments, or intracellular compartments. Elimination includes translocation (excretion) from a particular compartment or biotransformation (degradation).

The compounds which prolong the localized bioavailability of a nucleic acid may also achieve one or more of the following effects, due to their physical, chemical or rheological properties: (1) Protect nucleic acid, for example plasmid DNA, from nucleates due to viscosity effects; (2) increase the area of contact between nucleic acid, such as plasmid DNA, through extracellular matrices and over cellular membranes, into which the nucleic acid is to be taken up; (3) concentrate nucleic acid, such as plasmid DNA, at cell surfaces due to water exclusion; (4) indirectly facilitate uptake of nucleic acid, such as plasmid DNA, by disrupting cellular membranes due to osmotic, hydrophobic or lytic effects. The following polymers, oils and surfactants may be suitable for use as compounds which prolong the localized bioavailability of a nucleic acid: Celluloses, including salts of carboxymethylcelluloses, methylcelluloses, hydroxypropylcelluloses, hydroxypropylmethylcelluloses; salts of hyaluronates; salts of alginates; heteropolysaccharides (pectins); poloxamers (Pluronics); poloxamines (Tetronics); ethylene vinyl acetates; polyethylene glycols; dextrans; polyvinylpyrrolidones; chitosans; polyvinylalcohols; propylene glycols; polyvinylacetates; phosphatidylcholines (lecithins); miglyols; polylactic acid; polyhydroxybutyric acid. These substances may be prepared as solutions, suspensions, gels, emulsions or microemulsions of a water/oil (w/o), water/oil/water (w/o/w), oil/water (o/w) or oil/water/oil (o/w/o) type. Oil suspensions of lyophilized nucleic acid, such as plasmid DNA may be utilized. Carriers for these oil suspensions include, but are not limited to, sesame oil, cottonseed oil, soybean oil, lecithins, Tweens, Spans and Miglyols. By "solutions" is meant water soluble polymers and/or surfactants in solution with nucleic acids. By "suspensions" is meant water insoluble oils containing suspended nucleic acids. By "gels" is meant high viscosity polymers containing nucleic acids. By "emulsion" is meant a dispersed system containing at least two immiscible liquid phases. Emulsions usually have dispersed particles in the 0.1 to 100 micron range. They are typically opaque and thermodynamically unstable. Nucleic acids in the water phase can be dispersed in oil to make a w/o emulsion. This w/o emulsion can be dispersed in a separate aqueous phase to yield a w/o/w emulsion. Alternatively, a suitable oil could be dispersed in an aqueous phase to form an o/w emulsion. A "microemulsion" has properties intermediate to micelles and emulsions and is characterized in that they are homogenous, transparent and thermodynamically stable. They form spontaneously when oil, water, surfactant and cosurfactant are mixed together. Typically, the diameter of the dispersed phase is 0.01 to 0.1 microns, usually of the w/o and o/w type.

The compounds which prolong the bioavailability of a nucleic acid may also interact or associate with the nucleic acid by intermolecular forces and/or valence bonds such as: Van der Waals forces, ion-dipole interactions, ion-induced dipole interactions, hydrogen bonds, or ionic bonds. These interactions may serve the following functions: (1) Stereoselectively protect nucleic acids from nucleases by shielding; (2) facilitate the cellular uptake of nucleic acid by "piggyback endocytosis". Piggyback endocytosis is the cellular uptake of a drug or other molecule complexed to a carrier that may be taken up by endocytosis. CV Uglea and C Dumitriu-Medvichi. Medical Applications of Synthetic Oligomers. In: Polymeric Biomaterials. Edited by Severian Dumitriu. Marcel Dekker, Inc. 1993, incorporated herein by reference. To achieve the desired effects set forth it is desirable, but not necessary, that the compounds which prolong the bioavailability of a nucleic acid have amphipathic properties; that is, have both hydrophilic and hydrophobic regions. The hydrophilic region of the compounds may associate with the largely ionic and hydrophilic regions of the nucleic acid, while the hydrophobic region of the compounds may act to retard diffusion of nucleic acid and to protect nucleic acid from nucleases. Additionally, the hydrophobic region may specifically interact with cell membranes, possibly facilitating endocytosis of the compound and thereby nucleic acid associated with the compound. This process may increase the pericellular concentration of nucleic acid. Agents which may have amphipathic properties and are generally regarded as being pharmaceutically acceptable are the following: Methylcelluloses, hydroxypropylcelluloses, hydroxypropylmethylcelluloses; heteropolysaccharides (pectins); poloxamers (Pluronics); poloxamines (Tetronics); ethylene vinyl acetates; polyethylene glycols; polyvinylpyrrolidones; chitosans; polyvinylalcohols; polyvinylacetates; phosphatidylcholines (lecithins); propylene glycol; miglyols; polylactic acid; polyhydroxybutyric acid; xanthan gum. Also, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

In one embodiment of the invention, the compound which prolongs the bioavailability of a nucleic acid is a sustained-release compound which may be administered to an organism or to cells in culture. The sustained-release compound containing a nucleic acid is administered to the tissue of an organism, for example, by injection. In one embodiment the tissue is preferably muscle tissue. In another embodiment the tissue is preferably a joint space. By "sustained-release compound" is meant a substance with a viscosity above that of an isotonic saline solution (150 mM NaCl) containing a nucleic acid; for example, DNA in saline at 1 mg/ml has a viscosity of 3.01 mPa·sec, DNA in saline at 2 mg/ml has a viscosity of 3.26 mPa·sec, DNA in saline at 3 mg/ml has a viscosity of 5.85 mPa·sec (Viscosity measurements were performed at 25° C. in a Brookfield DV-III Rheometer with a No. 40 Spindle at 75 rpm for 30 minutes). Preferably the sustained-release compound has a viscosity in the range of about 0.1–20,000 mPa·sec above that of a formulation in which isotonic saline is the carrier for a nucleic acid. More preferably the range is about 0.1–5000 mPa·sec above that of a formulation in which isotonic saline is the carrier for a nucleic acid. Even more preferably the range is about 0.1–1000 mPa·sec above that of a formulation in which isotonic saline is the carrier for a nucleic acid. By "sustained-release" is meant that nucleic acid is made available for uptake by surrounding tissue or cells in culture for a period of time longer than would be achieved by administration of the nucleic acid in a less viscous medium, for example, a saline solution.

In another embodiment, the compound which prolongs the bioavailability of a nucleic acid is a thermo-reversible gel. By "thermo-reversible gel" is meant a gel which is substantially liquid at temperatures below about 30° C. but forms a gel at temperatures above about 30° C. Administration of the thermo-reversible gel by, for example, injection is thereby facilitated if the gel is cooled so that it is in a substantially liquid state when injected. However, upon contact with the tissue of an organism which is at a temperature of above about 30° C. the viscosity of the thermo-reversible gel increases, thereby increasing the localized bioavailability of a nucleic acid formulated with the thermo-reversible gel.

In another embodiment of the present invention, the molecules of the compound which prolongs the localized bioavailability of a nucleic acid tend to orient themselves in the direction of an induced flow and as an applied force causing the flow is increased and the resistance of the compound to flow is decreased, lowering an initial viscosity of the compound. When the applied force is removed, the compound substantially reverts to its initial viscosity. In a preferred embodiment the compound utilized is a salt of carboxymethylcellulose, such as sodium carboxymethylcellulose. Sodium carboxymethylcellulose has been used by the cosmetics, food, and pharmaceutical industries as a stabilizer, thickener, gelling agent, suspending agent, and a lubricant. Sodium carboxymethyl cellulose is an approved pharmaceutical excipient.

In another embodiment, the compound which prolongs the bioavailability of a nucleic acid is polyvinylpyrrolidone (PVP). PVP is a polyamide that forms complexes with a wide variety of substances and is chemically and physiologically inert. Specific examples of suitable PVP's are Plasdone-C®15, MW 10,000 and Plasdone-C®30, MW 50,000.

In another embodiment the compound which prolongs the bioavailability of a nucleic acid is an oily suspension. By "oily suspension" is meant a coarse dispersion containing finely divided insoluble material suspended in a liquid medium. These formulations include: nucleic acids, polymers, peptides or sugars and are dispersed with the aid of a dispersing agent, such as a surfactant in a suitable vehicle such as an oil. For example, DNA/PVP powder blend in Miglyol with 0.1% Tween-80, DNA/PVP powder blend in sesame oil with 0.1% Tween-80, DNA/lactose powder blend in Miglyol with 0.1% Tween-80, DNA complex powder blends in Miglyol with 0.1% Tween-80, where the DNA complex could comprise condensed DNA complexes such as DNA:polymer or DNA:peptide.

In another embodiment the compound which prolongs the bioavailability of a nucleic acid is a water-in-oil microemulsion. Examples would include: lecithin:sesame oil:butanol (surfactant/oil/cosurfactant) as the oil phase with DNA in saline as the water phase; lecithin:sesame oil:butanol (surfactant/oil/cosurfactant) as the oil phase with DNA complex saline as the water phase.

In another embodiment the compound which prolongs the bioavailability of a nucleic acid is a hydrogel. Nucleic acids may be loaded into hydrogels by placing swellable hydrogel systems in nucleic acid solutions. Swellable hydrogels include but are not limited to hydroxyethylmethacrylate (HEMA), polyethyleneglycolmethacrylate (PEGMA), cellulose ether hydrogels, comprising cross-linked hydroxypropyl cellulose, methyl cellulose, and hydroxypropylmethyl cellulose; calcium-crosslinked alginate; crosslinked polyvinyl alcohols and Poloxamers (Pluronics).

In another embodiment the compound which prolongs the bioavailability of a nucleic acid is a cationic polymer, such as Eudragit, Chitosan and Poloxamines (Tetronics). In another embodiment the compound which prolongs the bioavailability of a nucleic acid is a surfactant which forms micelles, such as Tween 80.

In another embodiment the uptake of nucleic acids in vitro, for example, cells in tissue culture is enhanced by the use of the compounds disclosed herein.

Other and further objects, features, and advantages will be apparent from the following description of the presently preferred embodiments in the invention.

Figure 1:
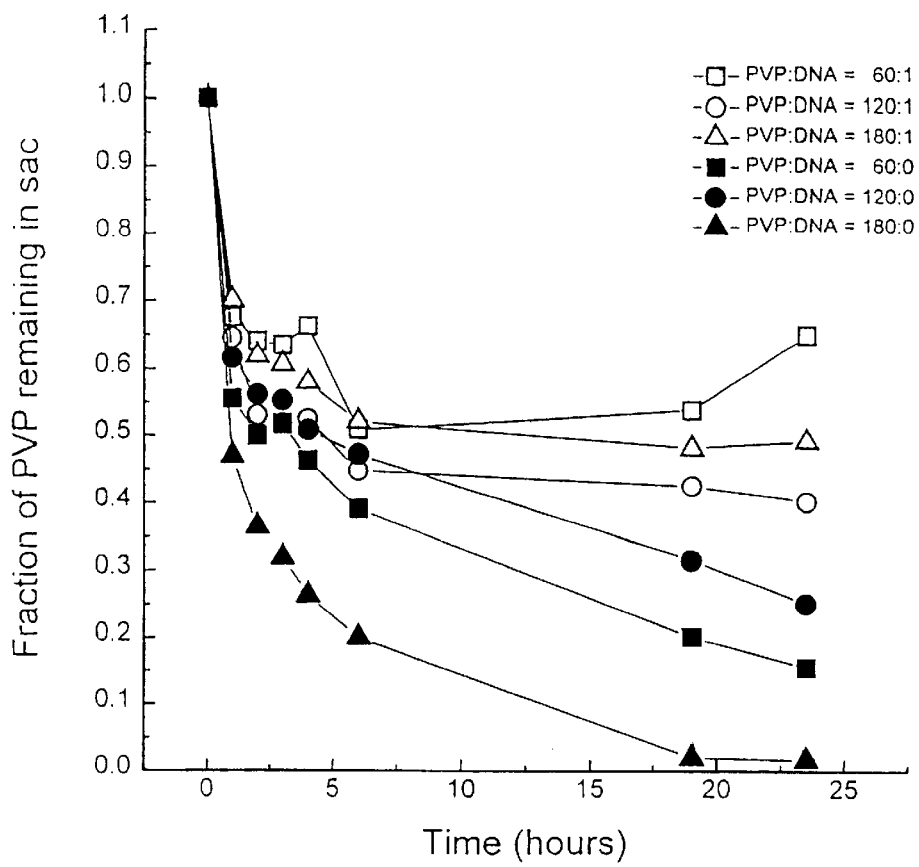
FIG. 1 illustrates a plot of the fraction of PVP:DNA at different ratios remaining within a dialysis sac over time.
Figure 2:
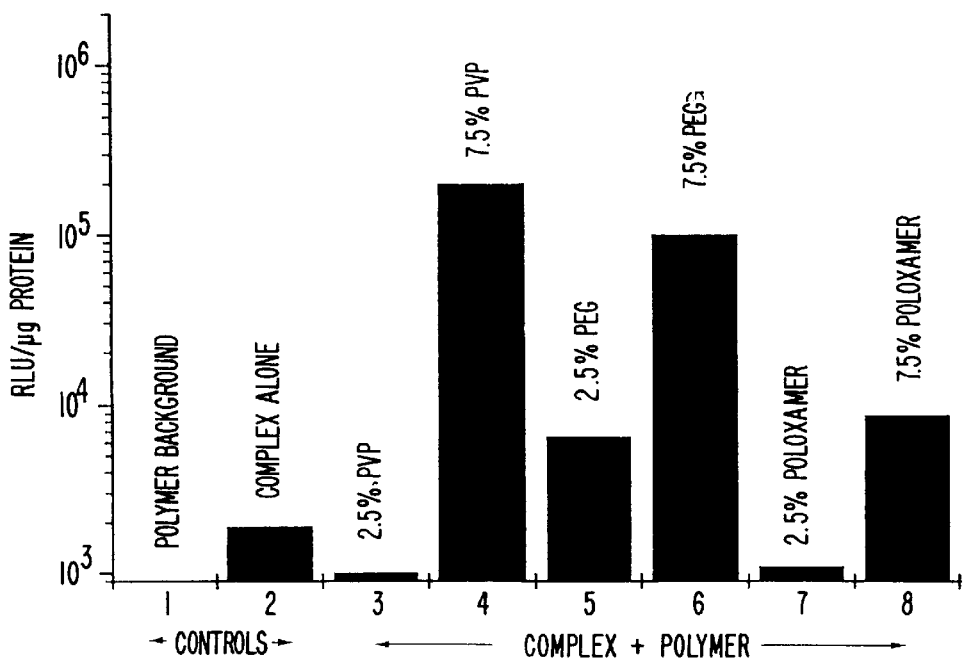
FIG. 2 illustrates the transfection efficiency into $C_2C_{12}$ myoblasts of a plasmid DNA complex administered with various polymers and controls comprising a polymer alone, and a PDNA complex alone.

The drawings are not necessarily to scale. Certain features of the invention may be exaggerated in scale or shown in schematic form in the interest of clarity and conciseness.

DETAILED DESCRIPTION OF THE INVENTION

Sodium carboxymethylcellulose is a long chain cellulose ether polymer. Many types are commercially available varying as to molecular weight (degree of polymerization) and percent carboxymethyl esterification per 10 cellulose units (degree of substitution). When mixed with water the polymers form viscous solutions which possess unique Theological characteristics. Polymerized types of cellulose ethers exhibit pseudoplastic and thixotropic behavior. By thixotropic behavior is meant that the long-chain molecules tend to orient themselves in the direction of flow; as the applied force is increased, the resistance to flow is decreased. Yet when high shear stress is removed, the solution will quickly revert to its original viscous state. Some celluloses exhibit thixotropic behavior wherein the solution returns to its viscous state over a period of time. The pseudoplasticity and thixotropic properties of sodium carboxymethylcellulose can be utilized for intramuscular injection of nucleic acid, such as plasmid DNA. A formulation of the viscous solution of sodium carboxymethylcellulose in isotonic saline containing plasmid DNA becomes fluid due to the pressure of injection by a syringe and needle then thicken once deposited in the muscle. The thickening of the injected formulation in situ provides retention of the expression vector within the muscle resulting in a controlled and sustained release and an enhanced uptake of the vector by the muscle cells.

In an alternative embodiment a thermoreversible gel may be used. After i.m. administration, plasmid DNA is maintained within the muscle by using a thermoreversible gel formulation. The use of compounds that are aqueous at ambient temperature, yet are gels at body temperatures (e.g. 37° C. for humans) are used to ease the formulation and administration of the DNA yet transition to and maintain the gel state for increased bioavailability at temperatures encountered in vivo. Such formulations (thermo-reversible gels) are prepared by adjusting the concentrations of polymers in aqueous solutions so that the vector delivery system will be liquid at room temperature or below and will be in the form of a gel in situ in the muscle at physiologic temperatures. Poloxamers (Pluronic F127®, Poloxamer 407®), poloxamines and the concentration of the polymers may be adjusted according to the formulation depending upon the route of administration (i.e., topical, i.m.,) for nucleic acid or nucleic acid complexes. These adjustments may be found in U.S. Pat. No. 5,292,516 which is incorporated by reference herein.

The following examples are offered by way of illustration and are not intended to limit the scope of the invention in any manner.

EXAMPLE 1
Demonstration of PVP Plasmid DNA Complex Formation

A given amount of lyophilized plasmid DNA is rehydrated with water and made isotonic with sterile 5M NaCl. After complete rehydration, an appropriate volume of sterile stock PVP solution in water is added to result in the desired final PVP concentration in isotonic saline. Alternatively, if plasmid DNA is already in solution, the appropriate volumes of plasmid DNA, 5M NaCl and stock PVP solutions are added to result in the desired proportions. The complex is allowed to form at 25° C. after gentle shaking. For example:

| Ingredient | Amount |
| --- | --- |
| lyophilized DNA | 1 mg |
| sterile water | 0.770 ml |
| 25% PVP in water | 0.2 ml |
| 5M NaCl | 0.030 ml |

Final formulation: 1 mg DNA/1 ml of 5% PVP in isotonic saline.

A dynamic dialysis experiment with three complexes was undertaken to determine the retention of PVP (MW=10 kDa) within dialysis sacs. Spectra/Por CE (cellulose ester) membranes with a MW cut-off of 25 kDa were employed. Three 1 ml formulations and corresponding controls were placed in pre-washed sacs, the sacs were closed and suspended in 100 ml saline at 25° C. The formulations and controls were as follows:

| | PVP/DNA (w/w) |
| --- | --- |
| Formulations | |
| 90 mg PVP and 0.5 mg CMV-β-gal in saline | 180:1 |
| 60 mg PVP and 0.5 mg CMV-β-gal in saline | 120:1 |
| 30 mg PVP and 0.5 mg CMV-β-gal in saline | 60:1 |
| Controls | |
| 90 mg PVP and 0.5 mg CMV-β-gal in saline | 180:0 |
| 60 mg PVP and 0.5 mg CMV-β-gal in saline | 120:0 |
| 30 mg PVP and 0.5 mg CMV-β-gal in saline | 60:0 |
| 0.5 mg CMV-β-gal in saline | 0:1 |

Aliquots were taken over 24 hours. The results are shown in FIG. 1. The fraction of PVP remaining in the dialysis sac was plotted over time. In all cases, the rate of PVP diffusion through the dialysis membrane was decreased in the presence of plasmid DNA, indicating complex formation between PVP and plasmid DNA at the three weight ratios tested. It was also determined that the sac volume remained constant during the duration of the experiment and that adherence of PVP to the membrane was negligible.

EXAMPLE 2
Demonstration of Increased Transfection Efficiency With Amphipathic Polymers It was demonstrated that amphipathic polymers such as PVP (MW=50 kDa), PEG (MW=8 kDa), and Poloxamer 407® can increase the efficiency of cell transfection, in-vitro in studies carried out using $C_2C_{12}$ myoblasts. Transfections were made using combinations of a complex and various polymers. The plasmid DNA complex consisted of plasmid DNA:condensing agent:Peptide 1 (1:64:3 −/+/−) (The condensing agent may be those as are known in the art, for example, dendrimers or polylysine). (Peptide-1 is a lytic peptide. A peptide similar to Peptide 1 is described in U.S. patent application Ser. No. 07/913,669, filed Jul. 14, 1992). The results show that at higher concentrations, 7.5% of the amphipathic polymers: PVP; PEG; and Poloxamer, the transfection efficiency of the plasmid DNA complex was significantly enhanced over the plasmid DNA complex alone or the polymers alone. Conversely, with the largely ionic polymer, CMC, the synergistic effect was not observed. This may have been due to destabilization of the net positively charged plasmid DNA complex by the negatively charged CMC. While not being limited in scope by any theory set forth, several mechanisms of action of amphipathic polymers may account for the observed results including: Stabilization of plasmid DNA complexes due to coating; increased cell membrane permeability, thereby allowing easier passage of the plasmid DNA complex through the cell; membrane and/or volume exclusion, increasing the concentration of plasmid DNA complexes at the cell surface. Poloxamer 407® has been shown to improve the transduction efficiency of adenoviral vectors by apparently maintaining a high pericellular concentration of the vector or by disrupting the cell membrane. K. March et al. Facilitation of Adenoviral Gene Delivery by Poloxamer 407®. Proceed. Intern. Symp. Control. Rel. Bioact. Mater., 21 (1994).

Figure 3:
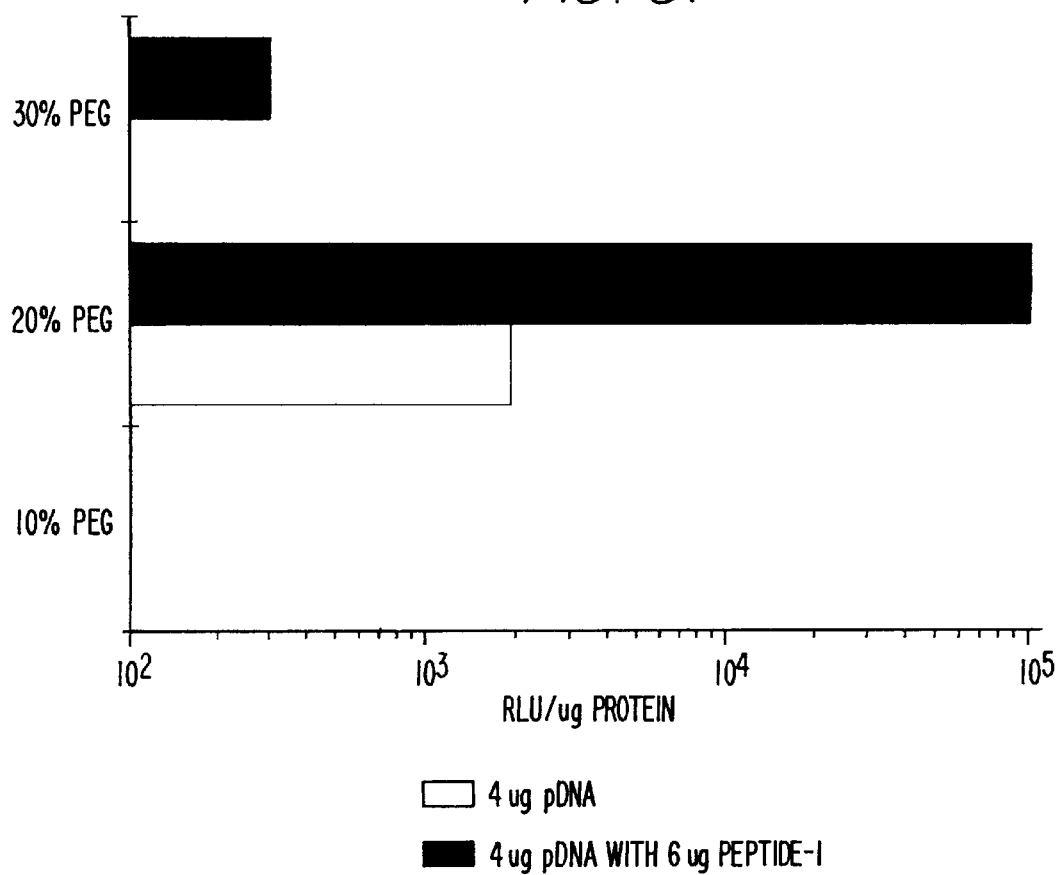
FIG. 3 illustrates the transfection efficiency into $C_2C_{12}$ myoblasts when transfected with plasmid DNA in 10%, 20%, and 30% PEG (8 kDa) with and without the presence of an endosomal release peptide (lytic peptide).

EXAMPLE 3
Demonstration of Increased Transfection Efficiency Utilizing a Lytic Peptide $C_2C_{12}$ myoblasts were transfected with 4 um plasmid DNA in 10%, 20%, and 30% PEG (8 kDa) with and without the presence of 6 ug of an endosomal release peptide (lytic peptide) The results are shown in FIG. 3. With no lytic peptide, only at 20% PEG as a carrier did transfection result. 10% and 30% PEG carriers did not give transfection. Additionally, when the lytic peptide was included, the transfection efficiency was enhanced 100-fold for the 20% PEG carrier. This result suggested the importance of a lytic agent in the carrier system, but also that the plasmid DNA in 20% PEG (without the peptide) was probably being taken up by the cell but degraded in the lysosomes. It has been found that 20% PEG is optimal for transfecting Micromonospora with bacteriophage DNA. J L Caso et al. Transfection in Micromonospora. Appl. Environ. Microbiol. 1987; 53 (10): 2544–47. The ability of the 20% PEG carrier to transfect cells is attributed to its ability to interact with plasmid DNA. Hydrodynamic light scattering data has shown that 20% PEG but not 10% PEG or 30% PEG can collapse plasmid DNA, presumably due to water exclusion.

EXAMPLE 4
Demonstration of Enhanced Nucleic Acid Uptake and Expression Utilizing PVP Polyvinylpyrrolidone (PVP) is a polyamide that forms complexes with a wide variety of substances and is chemically and physiologically inert. Applicants have shown that PVP enhances nucleic acid uptake/expression in muscle and should prove useful in delivering nucleic acids for the prophylactic treatment of diseases.

A CMV-β-galactosidase expression vector system was formulated in saline or 5% PVP and administered into the tibialis muscle of a rat. The activity of β-galactosidase gene product was measured in muscle extract at various time intervals after injection.

Delivery of DNA-PVP Formulation into Muscle

5–6 week old male rats (Fisher 344 strain, 120–130 g) from Harlan Sprague-Dawley laboratories were used. The animals were housed in microisolators at Baylor Animal Facility and maintained on a 12 h/12 h day/night cycle, with room temperature at 72° F., and at 40% humidity. Animals were anesthetized with a mixture of Ketamine (42.8 mg/ml), Xylazine (8.6 mg/ml) and Acepromazine (1.4 mg/ml) at a dose of 0.5–0.7 ml/kg, i.m. A 2–4 mm incision was made aseptically and 50 µl of a DNA formulation in PVP or saline was injected into the tibialis muscle of both legs. At various time intervals after injection, animals were anaesthetized, sacrificed by thoracotomy and the tibialis muscle was harvested and collected on dry ice and stored at −70° C. until assayed for β-galactosidase activity.

Extraction and Measurement of β-Galactosidase Activity in Muscle Injected with DNA-PVP Formulation β-galactosidase was extracted with 1.5 ml of Tris-EDTA-NaCl buffer containing the protease inhibitors leupeptin (1 µM), pepstatin (1 µM) and PMSF (0.25 mM). The extract was centrifuged at 13 K rpm for 15 min at 4° C. The supernatant was collected and 100 µg protein was assayed for β-galactosidase activity using a chemiluminescence detection system. An example of a suitable system is the Galacto-Light™ or Galacto-Light Plus™ available from Tropix, Inc. of Bedford, Mass. Galacto-Light™ and Galacto-Light Plus™ are a chemiluminescent reporter assay systems designed for the rapid, sensitive, and non-isotropic detection of β-galactosidase in cell lysates. The Galacto-Light™ (Galacto-Light plus™) reporter assay incorporates Galacton™ (Galacton-plus™) chemiluminescent substrate for β-galactosidase with Emerald™ luminescence enhancer. The chemiluminescent assay has a wide dynamic range, enabling detection of 2 fg to 20 ng of β-galactosidase. Jain, V., and I. Magrath. A Chemiluminescent Assay for Quantitation of β-Galactosidase in the Femtogram Range: Application to Quantitation of β-Galactosidase in lacZ-Transfected Cells. Anal. Biochem. 199: 119–124 (1991) incorporated herein by reference. Galacton™ chemiluminescent substrate has a half-life of light emission of approximately 4.5 minutes after the addition of Galacto-Light™ accelerator. It is suited for use with luminometers with automatic injectors and other instrumentation in which light emission measurements can be taken within a short period of time. Luminometer measurements taken within a narrow time frame make results more accurate and simple to interpret. Galacton-plus™ chemiluminescent substrate emits light which persists at a constant level for up to 60 minutes after the addition of Galacto-Light™ accelerator. This substrate is ideal for use with either plate luminometers that do not have automatic injection capabilities or with scintillation counters. Cell lysate or purified β-galactosidase is incubated with reaction buffer for 15 minutes to 1 hour. Galacton™ (Galacton-plus™) chemiluminescent substrate present in the reaction buffer is cleaved by the enzyme. The sample is then placed in a luminometer chamber and a light emission accelerator is added which terminates the β-galactosidase activity and accelerates light emission. Light output is quantitatively measured using a 5 second integral. It is important to stay within the linear range of the assay, especially if β-galactosidase is being used to normalize transfections. High signals can potentially saturate a photomultiplier tube resulting in artificially low signals. In addition, low signals that approach background levels may also be outside the linear range. In these cases, the amount of cell extract used in the assay should be adjusted to bring the assay within the linear range. The Galacto-Light™ (Galacto-Light Plus™) system has been formulated for luminometers with a 300 µl automatic injector. When using Galacto-Light™, manual injection may be performed if luminescence intensities are measured at approximately the same interval after adding the light emission accelerator to each sample. However, Galacto-Light plus™ eliminates this need due to the long half-life of light emission exhibited by Galacton-plus™. Reaction components should be scaled down if a luminometer with a smaller volume injector is used, however, sensitivity may be affected slightly. For plate luminometers it will be necessary to scale down the reaction volumes proportionately. However, it is recommended to keep the volume of cell extract between 5 and 20 µl. The Lysis solution included with the kit may be substituted with alternative lysis solutions and lysis procedures. This may be desirable if assays for other co-transfected reporters require specific assay buffers. Alternative lysis solutions should be compared with the Galacto-Light™ Lysis Solution to ensure optimal performance of the assay. Chemiluminescent reporter assays may be conducted in cells or tissues that have endogenous β-galactosidase activity. Endogenous enzyme activity is slightly reduced at the pH of the Galacto-Light™ Reaction Buffer, while bacterial β-galactosidase encoded on transfected plasmids is only slightly affected. In this case, it is important to assay the level of endogenous enzyme with non-transfected cell extracts. Significant reductions of endogenous activity can be achieved using heat inactivation. Tissue extracts may also require the use of protease inhibitors. The following reagents are used: Chemiluminescent Substrate: Galacton™ or Galacton-plus™ is a 100× concentrate which is diluted in reaction buffer diluent prior to use (store at 4° C. or optimally at −20° C.); Lysis Solution containing 100 mM potassium phosphate pH 7.8, 0.20% Triton X-100 (Store at 4° C.). Dithiothrietol (DTT) should be added fresh prior to use to a final concentration of 1 mM; Reaction Buffer Diluent containing 100 mM sodium phosphate pH 8.0, 1 mM magnesium chloride (store at 4° C.); Accelerator contains a ready-to-use luminescence accelerator reagent (store at 4° C.).

Preparation of Cell Extracts From Tissue Culture Cells (1) Aliquot the required amount of Lysis Solution. Add fresh DTT to 1 mM. (2) Rinse cells 2 times with 1×Phosphate Buffered Saline (PBS). (3) Add Lysis Solution to cover the cells (250 μl of Lysis Buffer for a 60 mm culture plate should be adequate). (4) Detach cells from culture plate using a rubber policeman or equivalent. Non-adherent cells should be pelleted and lysis buffer should be added sufficient to cover the cells. The cells should then be resuspended in the lysis buffer by pipetting. (5) Transfer cells to a microfuge tube and centrifuge for 2 minutes to pellet any debris. (6) Transfer supernatant to a fresh microfuge tube. Cell extracts may be used immediately or frozen at −70° C. for future use.

Chemiluminescent Detection Procedure

It is recommended that all assays are performed in triplicate. (1) Dilute Galacton™ (Galacton-Plus™) substrate 100-fold with Galacto-Light™ Reaction Buffer Diluent to make Reaction Buffer. This mixture will remain stable for several months if stored uncontaminated at 4° C.

It is recommended to only dilute the amount of substrate that will be used within a two month period. (2) Warm to room temperature the amount of Reaction Buffer required for the entire experiment. (3) Aliquot 2 to 20 μl of individual cell extracts into luminometer sample tubes. (The amount of cell extract required may vary depending on the amount of expression and the instrumentation used. Use 5 μl of extract for positive controls and 10 to 20 μl of extract for experiments with potentially low levels of enzyme. It is important to vary the concentrations of extract to keep the signal within the linear range of the assay.) (4) Add 200 μl of Reaction Buffer to a luminometer cuvette and gently mix. Incubate at room temperature for 60 minutes. Incubations can be as short as 15 minutes, but the linear range of the assay may decrease. (Measurements are time dependent. Reaction Buffer should be added to sample extracts in the same time frame as they are counted on the luminometer. For example, if it takes 10 seconds to completely count a sample, then Reaction Buffer should be added to tubes every 10 seconds.) (5) Place cuvette in a luminometer. Inject 300 μl of Accelerator. After a 2 to 5 second delay following injection, count the sample for 5 seconds. If manual injection is used, then the Accelerator should be added in the same consistent time frame as the Reaction Buffer is added. This is critical when using Galacton™.

Preparation of Controls

Positive Control

Add 1 μl of β-galactosidase (10 units/ml, Sigma Cat. No. G-5635 diluted in 0.1 M sodium phosphate pH 7.0, 1.0% BSA) to mock transfected cell extract equivalent to the volume of experimental cell extract used. Proceed with Chemiluminescent Detection Procedure.

Negative Control

Assay of volume of mock transfected cell extract equivalent to the volume of experimental cell extract used. Proceed with Chemiluminescent Detection Procedure.

Heat Inactivation of Endogenous β-qalactosidase

Some cell lines may exhibit relatively high levels of endogenous β-galactosidase activity. This may lead to background which will decrease the overall sensitivity of the assay by lowering the signal to noise ratio. A procedure for heat inactivation of endogenous β-galactosidase activity has been described by Young et al. Young, Dorothy C., S. D. Kingsley, K. A. Ryan, and F. J. Dutko. Selective Inactivation of Eukaryotic β-Galactosidase in Assays for Inhibitors of HIV-1 TAT Using Bacterial β-Galactosidase as a Reporter Enzyme. Anal. Biochem. 215:24–30 (1993), incorporated herein by reference. A modified version of this protocol has also been described by Shaper et al. in which a cocktail of protease inhibitors is used in conjunction with the heat inactivation procedure for reducing β-galactosidase in tissue extracts. Shaper, N., Harduin-Lepers, A., and Shaper, H. H. Male Germ Cell Expression of Murine β4-Galactosyltransferase. A 796-base pair genomic region containing two cAMP-responsive elements (CRE)-like elements, mediates expression in transgenic mice. J. Biol. Chem. 269:25165–25171 (1994), incorporated herein by reference.

Inactivation of β-Galactosidase Activity in Cell Extracts

The following procedures should be performed immediately prior to the Chemiluminescent Detection Procedure in the Preparation of Cell Extracts From Tissue Culture Section. (1) Following cell extract preparation, heat the extract to 48° C. for 50 minutes. (2) Proceed with Chemiluminescent Detection Procedure. (Although Young et al. suggest 50° C. for 60 minutes, heat inactivation at 48° C. for 50 minutes is suggested.)

Inactivation of Endogenous β-Galactosidase Activity in Tissue Extracts (1) To the Galacto-Light™ lysis buffer, add PMSF to a final concentration of 0.2 mM and leupeptin to a final concentration of 5 μg/ml just before use. (2) Heat inactivate the extracts by heating at 48° C. for 60 minutes. (3) Proceed with Chemiluminescent Detection Procedure. (AEBSF (Sigma Cat. No. A-5938) may be used in place of PMSF (Sigma Cat. No. P-7626). AEBSF is a water soluble serine protease inhibitor).

A liquid scintillation counter may be used as a substitute for a luminometer, however, sensitivity may be lower Fulton, R., and B. Van Ness. Luminescent Reporter Gene Assays for Luciferase and β-galactosidase Using a Liquid Scintillation Counter. BioTechniques 14(5): 762–763(1993), incorporated herein by reference. Nguyen, V. T., M. Morange, and O. Bensaude. Firefly Luciferase Luminescence Assays Using Scintillation Counters for Quantitation in Transfected Mammalian Cells. Anal. Biochem. 171:404–408 (1988), incorporated herein by reference. The results are expressed as mean +/− S.E.M of Relative Light Unit, as indicative of b-galactosidase activity, per 100 ug muscle protein. When using a scintillation counter, it is necessary to turn off the coincident circuit in order to measure chemiluminescence directly. The manufacturer of the instrument should be contacted to determine how this is done. If it is not possible to turn off the coincident circuit, a linear relationship can be established by taking the square root of the counts per minute measured and subtracting the instrument background. Actual=(measured-instrument background)$^{1/2}$. Other methods of measuring a chemiluminescent signal as are known in the art may also be utilized.

Results

Figure 4:
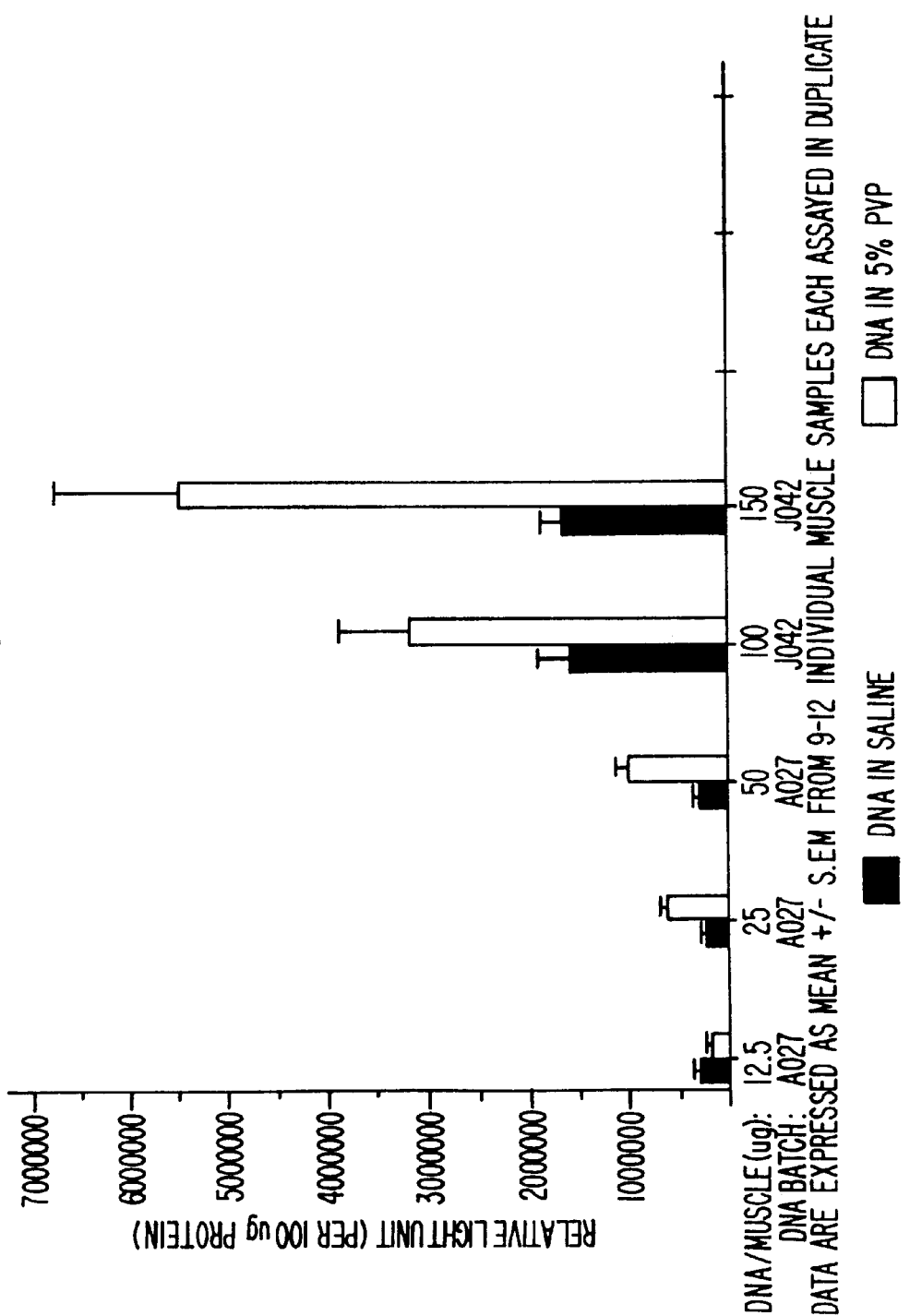
FIG. 4 illustrates the magnitude of β-galactosidase marker gene expression when a plasmid containing the marker gene is administered in saline or a PVP formulation.
Figure 5:
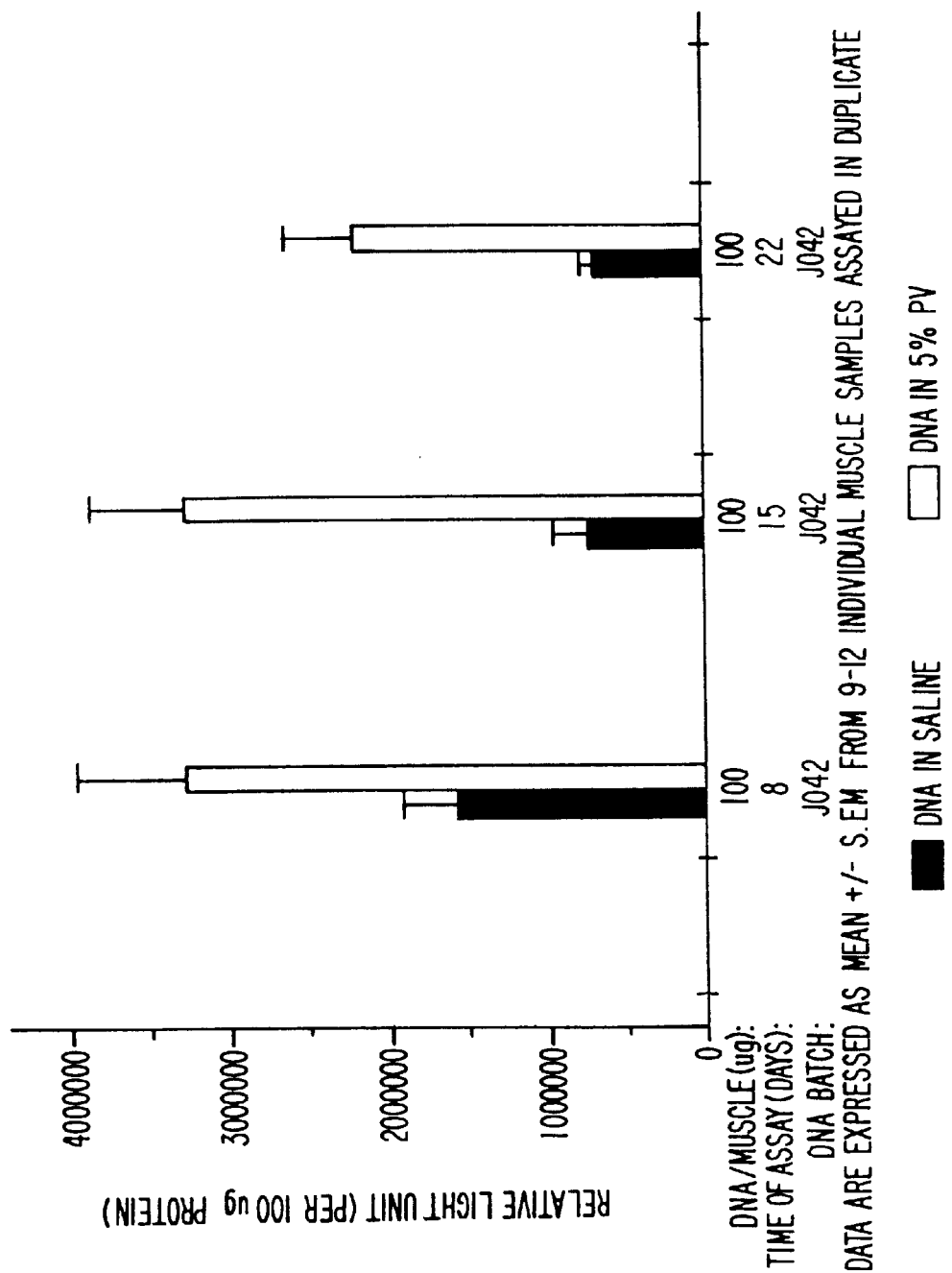
FIG. 5 illustrates the time course of β-galactosidase expression in PVP as compared to the time course in saline.
Figure 6:
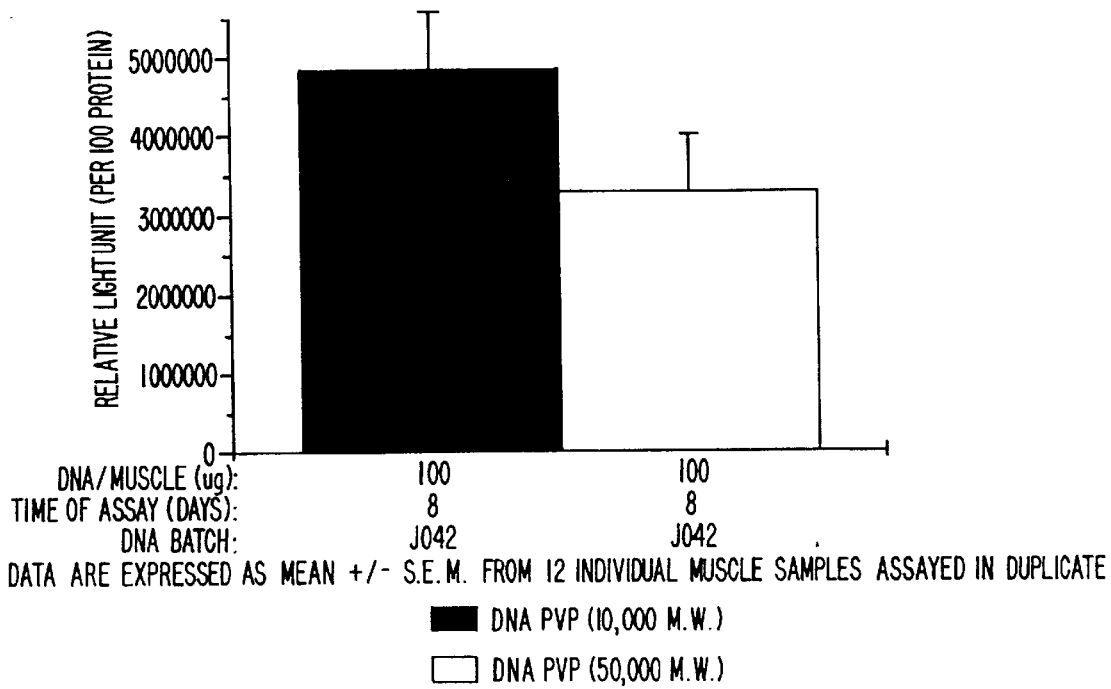
FIG. 6 illustrates that the biologically excretable low molecular weight PVP is equally effective as the high molecular weight species in transfecting muscle tissue.

Intramuscular administration of CMV-β-galactosidase expression vector formulated in either saline or 5% PVP (International Specialty Products, Plasdone-C®15, m.w. 10,000 and Plasdone-C®30, m.w. 50,000, Pharmaceutical grade) resulted in the expression of β-galactosidase enzyme in the transfected muscles. The magnitude and time course of β-galactosidase expression was compared between the saline and PVP formulations. As shown in FIG. 4, the magnitude of expression was considerably higher when the DNA was formulated in PVP (50,000 MW) as compared to saline. The enhancement of β-galactosidase expression by PVP over saline was dependent on the dose of DNA injected. At a low DNA dose (12.5 ug/injection) there was no difference in the expression level between PVP and saline formulations. At a higher DNA dose (25–150 ug) the level of expression in PVP was higher compared to saline formulation. The DNA dose response in saline formulation reached a plateau at 25 ug whereas it continued to increase in a linear fashion in PVP formulation in the dose range studied. To further characterize the DNA-PVP formulation, the time course of β-galactosidase expression in PVP was compared with the time course in saline. As shown in FIG. 5, the difference between PVP and saline formulations was maintained throughout the time course. Maximum difference was observed at day 15 after injection. Experiments were also conducted with low molecular weight PVP (10,000 daltons). As shown in FIG. 6, the biologically excretable low molecular weight PVP is equally effective as the high molecular weight species in transfecting muscle tissue. The high and low molecular weight PVP was administered at different concentrations, resulting in solutions with the same viscosity.

EXAMPLE 5

Physical Studies on PVP and PVP-DNA Interactions

PVP-DNA interactions by FTIR: Fourier-Transformed Infra Red (FTIR) has been used to investigate PVP-DNA interactions. From this study, it has been shown that PVP stabilizes the backbone of the DNA, as indicated by the sharpness of bands 970 cm$^{-1}$ and 1086 cm$^{-1}$. The FTIR also suggests a decrease in the resonance character of the bases. There is also a broadening and decrease in intensity from 1400–1600 cm-1 and increased resolution and intensity from 1650–1800 cm$^{-1}$ and 1200–1400 cm$^{-1}$. This is interpreted as a decrease in resonance character associated with the DNA bases when PVP is present. The result is the formation of explicit double and single bond formation. The FTIR (>1650 cm–1) also suggests a greater distinction in the environment between exocyclic base residues due to splits in the degeneracy when the PVP is present. Alternatively, the apparent splits may result from the presence of the carbonyl stretching mode associated with PVP.

Mechanism of Action: While the invention is not to be limited by any particular theory, as mechanisms of action, it is postulated that PVP may act as follows:

1. It may protect the DNA by altering the diffusion of nucleases within the polymer matrix. It may also provide water exclusion which may reduce nuclease activity. Consistent with a physical interaction between DNA and PVP, isothermal titration calorimetry measurements using a Hart Scientific microtitration calorimeter gave a positive heat of binding. These measurements indicate a positive enthalpy and suggest that PVP:DNA interactions are driven by the displacement of water or counterions.

2. PVP, through its hydrophobic regions may be capable of interacting, even fusing with biological membranes.

3. When PVP is at the surface of the cell, it will concentrate the associated DNA at that surface. If PVP is also fusogenic, it could then transfer the localized DNA into the cytoplasm.

EXAMPLE 6

Protection of DNA from DNAse I Degradation

Figure 7:
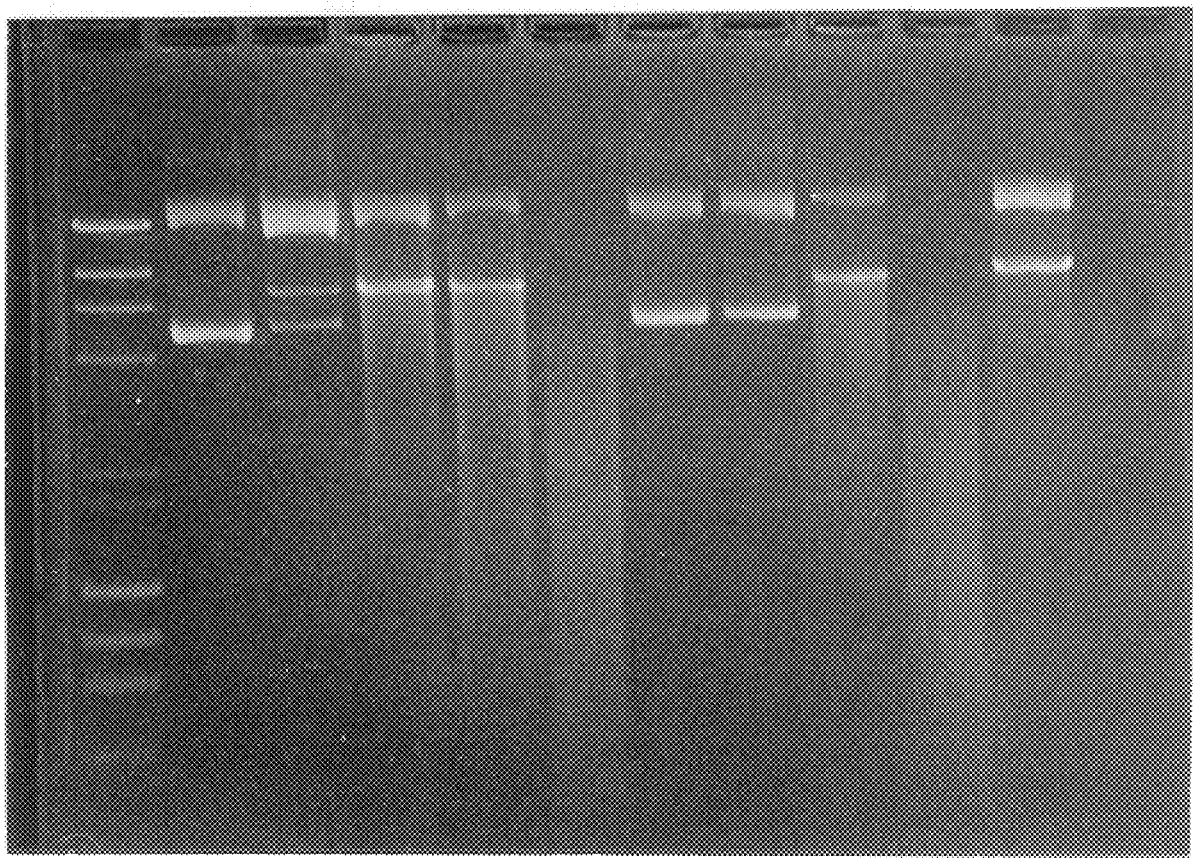
FIG. 7 is an illustration of the results of a gel-electrophoresis undertaken to quantitate the degree of DNA degraded by DNAse I in saline versus PVP.

Protection of DNA in formulation compositions from DNAse I degradation by 5% PVP was demonstrated. Solutions of DNA alone or DNA in 5% PVP (50 kDa) were prepared at 37° C. in saline DNAse I Activity Buffer (50 mM sodium acetate, pH 6.5 with 10 mM $MgCl_2$, 2 mM $CaCl_2$). The concentration of DNA was 100 ug/ml of Activity Buffer. To all solutions, various amounts of DNAse I in Activity Buffer were added. The weight ratios of DNAse I to DNA were: 1:250,000, 1:50,000, 1:25,000, 1:12,000. The manufacturer of the DNAse I used indicates that 1:10,000 DNAse I to DNA will entirely degrade DNA at 37° C. in 15 minutes. The samples were allowed to incubate at 37° C. for 15 minutes, at which time an aliquot of each sample was added to tracking dye. As shown in FIG. 7, gel-electrophoresis was undertaken to quantitate the degree of degraded DNA. The results showed that higher amounts of DNAse I were needed to degrade DNA in the presence of PVP as compared to the absence of PVP.

EXAMPLE 7

Figure 8:
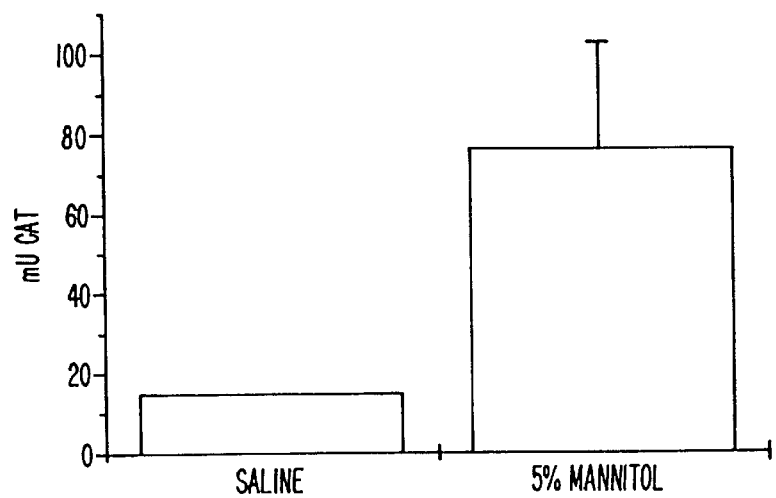
FIG. 8 is an illustration of the effect of administering DNA containing a CAT reporter gene in 5% mannitol versus saline.

Increase in Expression of a Reporter Gene Administered in Mannitol Versus Saline As shown in FIG. 8, the effect of administering DNA containing a chloramphenicol acetyltransferase (CAT) reporter gene in 5% mannitol versus saline was investigated. The use of CAT as a reporter gene is well known in the art. A typical protocol may be found in Current Protocols in Molecular Biology, Chapter 9, Unit 9.6A Reporter System Using Chloramphenicol Acetyltransferase © 1993 Current Protocols. As shown in FIG. 8, the expression of the CAT reporter gene in 5% mannitol was approximately four times that when administered in saline. The DNA was administered to the tibialis muscle of rats as described above in Example 4.

EXAMPLE 8

Increase in Expression of a Reporter Gene Administered in PVA Versus Saline

Figure 9:
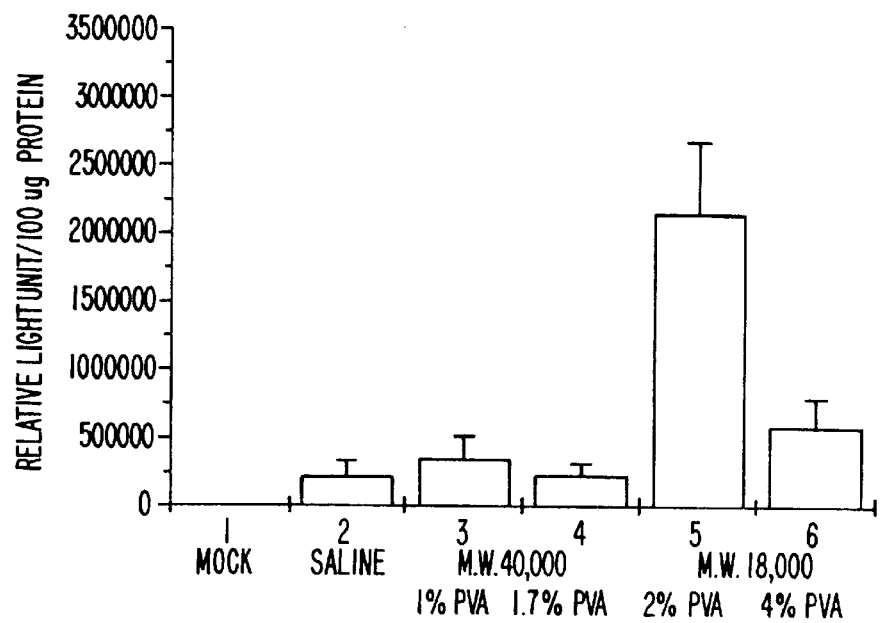
FIG. 9 is an illustration of the effect of administering PVA containing a CMV-β-galactosidase reporter gene in high molecular weight (40,000 daltons) at 1% PVA or 1.7% PVA and low molecular weight (18,000 daltons) at 2% PVA or 4% PVA.

As shown in FIG. 9, the effect of administering DNA containing a CMV-β-galactosidase reporter gene in high molecular weight PVA (40,000 daltons) at 1% PVA or 1.7% PVA and low molecular weight PVA (18,000 daltons) at 2% PVA or 4% PVA was investigated. The low molecular weight PVA at both 2% and 4% gave approximately two and six times expression, respectively, of the reporter gene as saline. Determination of the level of expression of the reporter gene was performed as described above in Example 4. The DNA was administered to the tibialis muscle of rats as described above in Example 4.

EXAMPLE 9

Figure 10:
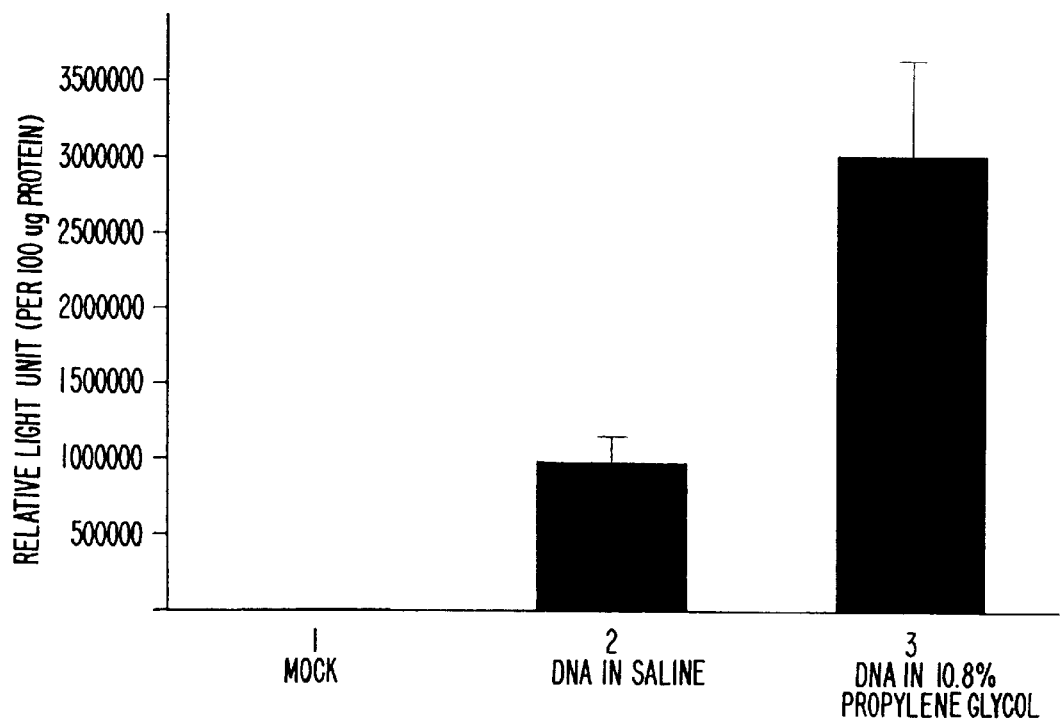
FIG. 10 shows the CMV-Beta-Glactosidase Expression in Tibialis Muscle. The graph shows a comparison of various gene delivery systems. Relative light units per 100 ug of protein are shown for (1) mock; (2) DNA in saline; and (3) DNA in 10.8% propylene gycol.

Increase in Expression of a Reporter Gene Administered in Propylene Glycol Versus Saline As shown in FIG. 10, the effect of administering DNA in 10.8% propylene glycol versus saline was investigated. As shown in that Figure, the expression of the CMV-β-galactosidase reporter gene in 10.8% propylene glycol was approximately three times that when administered in saline. Determination of the level of expression of the reporter gene was performed as described above in Example 4. The DNA was administered to the tibialis muscle of rats as described above in Example 4.

It will be readily apparent to one skilled in the art that various substitutions and modifications may be made to the invention disclosed herein without departing from the scope and spirit of the invention.

What is claimed is:

1. A method of administering to a mammal a composition for delivery of a nucleic acid molecule to a muscle tissue, comprising the step of injecting said composition into a muscle tissue of a mammal, wherein said composition prolong the bioavailability of a nucleic acid molecule and comprises in solution form, an amphiphilic compound admixed with a nucleic acid molecule, wherein said compound is polyvinyl pyrrolidone, polyvinyl alcohol, polyethylene glycol or propylene glycol, wherein said compound enhances the delivery of said nucleic acid to muscle cells in vivo, and wherein said nucleic acid molecule comprises a sequence encoding a gene product.

2. The method of claim 1, wherein said nucleic acid molecule is a deoxyribonucleic acid molecule.

3. The method of claim 1, wherein said gene product is a polypeptide or protein.

4. The method of claim 1, wherein said compound is polyvinyl pyrrolidone.

5. The method of claim 1, wherein said compound is polyvinyl alcohol.

6. The method of claim 1, wherein said compound is polyethylene glycol.

7. The method of claim 1, wherein said compound is propylene glycol.

8. The method of any one of claims 1–7 wherein said composition consists essentially of said compound and said nucleic acid molecule.

9. The method of any one of claims 1–7 wherein said composition consists of said compound and said nucleic acid molecule.

* * * * *